(12) United States Patent
Gritton

(10) Patent No.: US 12,194,773 B1
(45) Date of Patent: Jan. 14, 2025

(54) FRAGRANCE EMITTING WRITING UTENSIL

(71) Applicant: Samuel Bond Gritton, Louisville, KY (US)

(72) Inventor: Samuel Bond Gritton, Louisville, KY (US)

(*) Notice: Subject to any disclaimer, the term of this patent is extended or adjusted under 35 U.S.C. 154(b) by 0 days.

(21) Appl. No.: 18/134,593

(22) Filed: Apr. 14, 2023

Related U.S. Application Data

(60) Provisional application No. 63/332,603, filed on Apr. 19, 2022.

(51) Int. Cl.
*B43K 29/00* (2006.01)
*A61L 9/12* (2006.01)

(52) U.S. Cl.
CPC .............. *B43K 29/00* (2013.01); *A61L 9/127* (2013.01); *A61L 2209/133* (2013.01)

(58) Field of Classification Search
CPC .... B43K 19/00; A61L 9/127; A61L 2209/133
USPC ........................................................ 401/195
See application file for complete search history.

(56) References Cited

U.S. PATENT DOCUMENTS

| | | |
|---|---|---|
| 2007/0020033 A1 | 1/2007 | Walsh |
| 2007/0269256 A1 | 11/2007 | Dubinski |
| 2015/0197118 A1* | 7/2015 | Wagenheim ........... B43K 24/06 29/428 |
| 2016/0106243 A1 | 4/2016 | Coutu et al. |
| 2017/0136805 A1 | 5/2017 | Hoffman |
| 2019/0047316 A1 | 2/2019 | Takagi et al. |
| 2019/0241007 A1 | 8/2019 | Steed |

FOREIGN PATENT DOCUMENTS

| | | | | |
|---|---|---|---|---|
| CN | 205058948 U | * | 3/2016 | |
| JP | H08337091 A | * | 12/1996 | |
| JP | 2007237722 A | * | 9/2007 | |
| KR | 200300721 Y1 | * | 1/2003 | ............. B43K 29/00 |
| WO | WO-2006052092 A1 | * | 5/2006 | ............. B43K 23/12 |

OTHER PUBLICATIONS https://www.amazon.com/vdp/700d78b79cc44f9dafd35a922e52805e. Printed Apr. 14, 2023.
https://www.gps-edu.com/shop/store/essential_oils-products/aromapen/. Printed Apr. 14, 2023.
https://www.etsy.com/listing/865024524/pens-that-make-scents-purple?ga_order-most_relevant&ga_search_type=all&ga_view_type=gallery&ga_search_query=essential+oil+pen&ref=sr_gallery-1-3&sts=1&organic_search_click=1. Printed Apr. 14, 2023.
https://www.sb-designstudio.com/product/Essential-Oil-Diffuser-Pen-Rose-G2762. Printed Apr. 14, 2023.

* cited by examiner

*Primary Examiner* — Jennifer C Chiang
(74) *Attorney, Agent, or Firm* — Joseph E. Maenner; Maenner & Associates, LLC

(57) ABSTRACT

A writing instrument includes an elongate hollow body having a distal tip and a proximal end portion, a marking medium located at least partially inside the hollow body and extendible from the distal tip, and a scent substrate in the proximal portion of the hollow body. An inner cap is disposed over the proximal portion. The cap has at least one scent opening. An outer cap is disposed over the inner cap such that rotation of the outer cap relative to the inner cap to a first position covers the at least one scent opening and rotation of the outer cap relative to the inner cap to a second position reveals the at least one scent opening.

11 Claims, 6 Drawing Sheets

FRAGRANCE EMITTING WRITING UTENSIL

BACKGROUND OF THE INVENTION

Field of the Invention

The invention relates to writing instruments. More particularly, this invention relates to a writing instrument emitting a fragrance and having the function of being able to allow or prevent fragrance from emitting, increase the strength of the fragrance, and change the fragrance to a different fragrance.

Description of the Related Art

Fragrance emitting writing utensils are known. However, known fragrance emitting writing utensils are not capped and the emission of the scent cannot be controlled.

It would be beneficial to provide a fragrance emitting writing utensil that allows the fragrance emitting portion to be partially or totally closed to reduce or eliminate the amount of fragrance being emitted as desired by a user without the need to remove material from the utensil, such as a removable cap that can be lost or damaged when removed.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is a writing instrument including an elongate hollow body having a distal tip and a proximal end portion, a marking medium located at least partially inside the hollow body and extendible from the distal tip, and a scent substrate in the proximal portion of the hollow body. An inner cap is disposed over the proximal portion. The cap has at least one scent opening. An outer cap is disposed over the inner cap such that rotation of the outer cap relative to the inner cap to a first position covers the at least one scent opening and rotation of the outer cap relative to the inner cap to a second position reveals the at least one scent opening.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION

Figure 1:
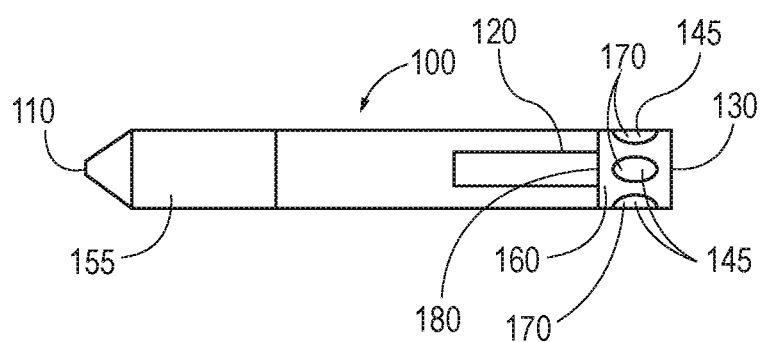
FIG. 1 is a section view of a utensil with a fragrant object and rotational cap to prevent or allow aroma to emit.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

The word "about" is used herein to include a value of +/−10 percent of the numerical value modified by the word "about" and the word "generally" is used herein to mean "without regard to particulars or exceptions."

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

The present invention is a writing utensil such as a ballpoint pen or mechanical pencil that is capable of emitting fragrance, increasing the strength of said fragrance, changing the fragrance that is emitted, turning on and off fragrance at will, without necessarily having to remove anything from the utensil and replacing the object creating the fragrance. The invention may feature a fragrant object encased within the utensil and a cap of the utensil having concavities to allow the aroma to emit. The concavities can be opened or closed at will to allow or prevent fragrance from emitting.

Referring to FIG. 1, there is generally shown a fragrance utensil 100 that emits fragrance 180 from fragrant object 120. Fragrant object 120 may be made of absorbing materials such as cotton, wool, polymer, stone, among others. The fragrant object 120 may be solid or liquid. The fragrant object 120 may be innately fragrant or a material that can effectively absorb fragrant additives such as chemical additives, essential oils, or others. When side-cap holes 145 within side-cap 160 are rotated to be aligned with utensil holes 170 (more visible in FIG. 2) fragrance 180 travels from fragrant object 120 through utensil holes 170 and side-cap holes 145 into the air. When side-cap holes 145 are rotated so as not to be aligned with utensil holes 170, fragrance 180 travels from fragrant object 120 through utensil holes 170, but does not travel further outward as fragrance 180 is met by the solid structure of side-cap 160 that has been rotated. Fragrance Utensil 100 extends marking material tip 110 by twisting twist material 155.

Figure 2:
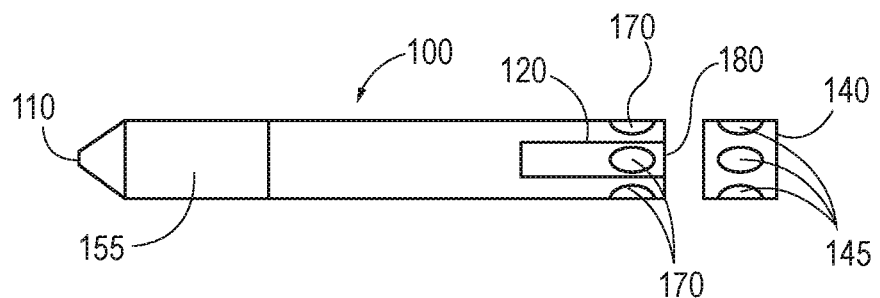
FIG. 2 is a section view of a utensil with the rotational cap detached to showcase the utensil holes previously concealed by the attached cap.

Referring to FIG. 2, generally shown fragrance utensil 100 is shown with detached cap 140 to highlight utensil holes 170. Fragrant object 120 is present along with marking material tip 110, twist material 155, fragrance 180, and side-cap holes 145.

Figure 3A:
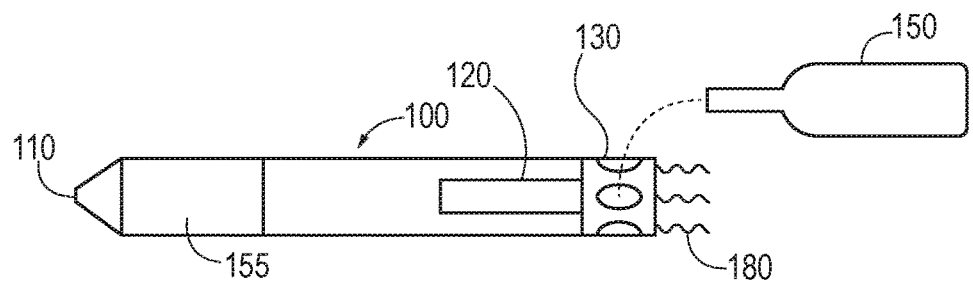
FIG. 3a is a section view of fragrance additives being added to attached side-cap.
Figure 3B:
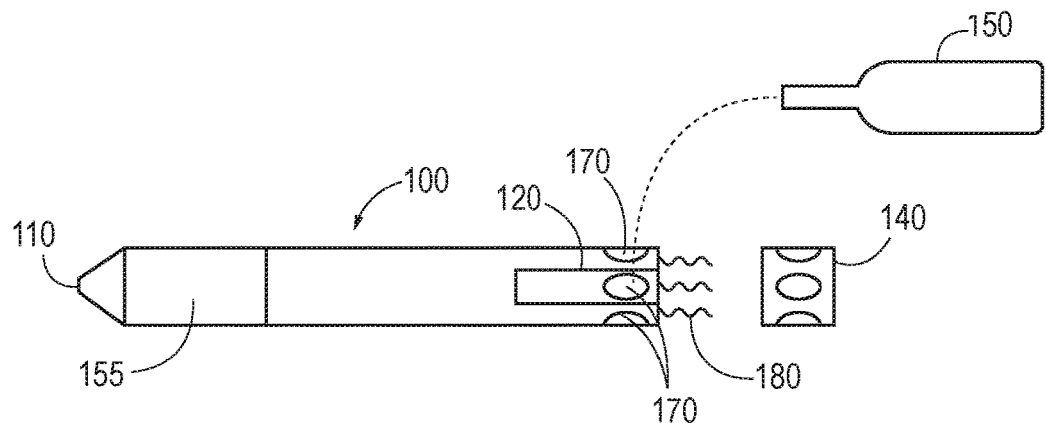
FIG. 3b is a section view of fragrance additives being added to utensil holes.
Figure 3C:
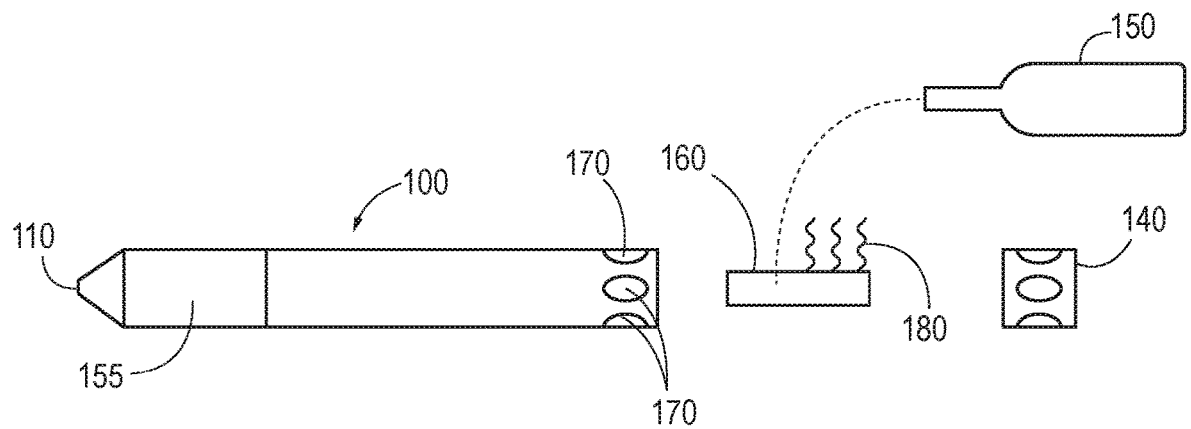
FIG. 3c is a section view of fragrance additives being added to removed fragrant object.

Referring to FIGS. 3a, 3b, and 3c, fragrance utensil 100 can have the strength of fragrance 180 increased or the properties of fragrance 180 changed using essential oil additives or other chemical additives 150. Fragrance utensil 100 in FIGS. 3a, 3b, and 3c has twist material 155, and marking material 110. Additives 150 can be applied to 3 different areas.

Referring to FIG. 3a, the first area additive 150 can be applied is to side-cap 130 attached to the utensil 100.

Referring to FIG. 3b, the second place additives 150 can be added is to utensil holes 170 when detached cap 140 is detached from utensil 100.

Referring to FIG. 3c, the third place additives 150 can be added to is directly to removed fragrant object 160.

Figure 4:
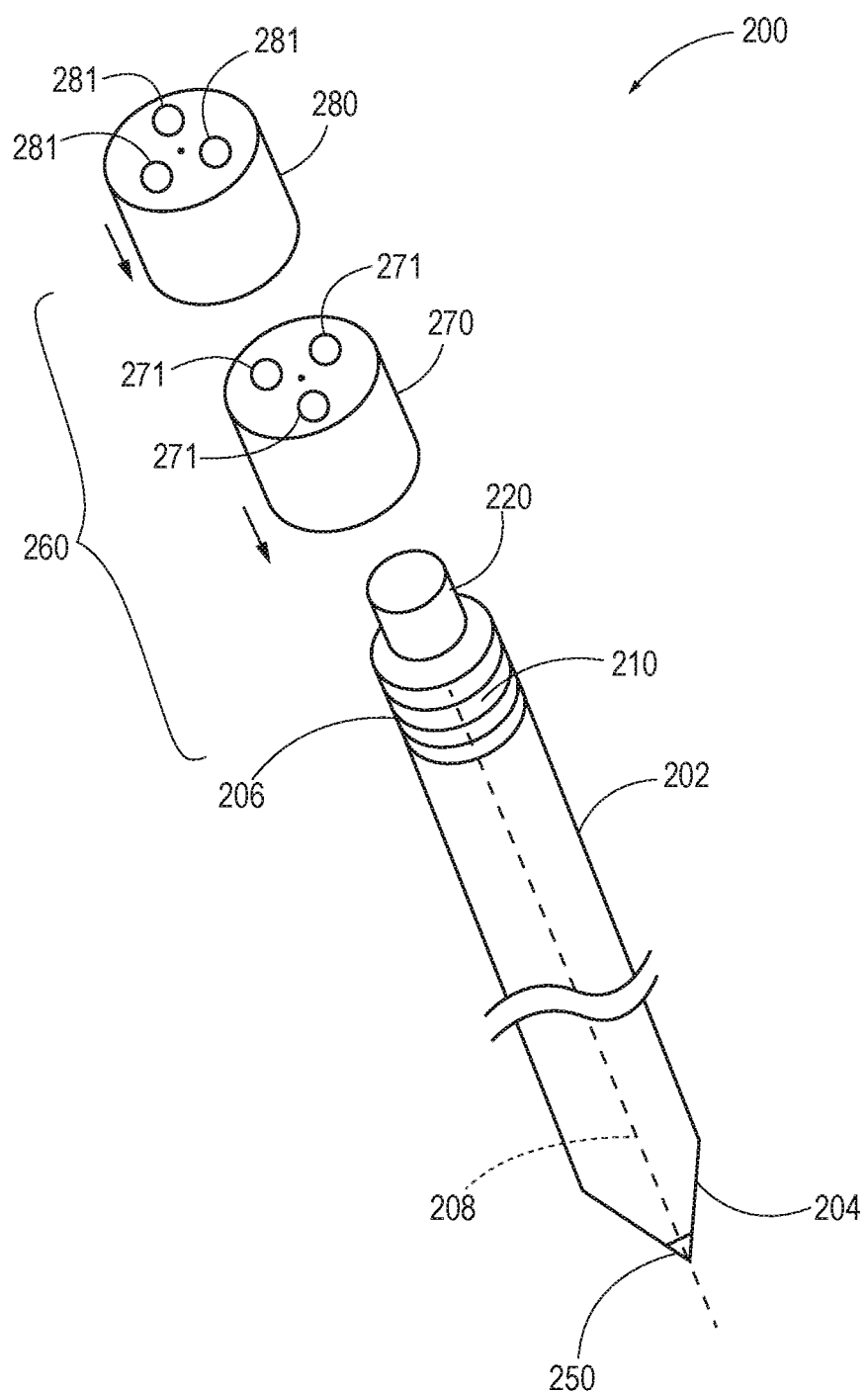
FIG. 4 is a section view of a utensil with a fragrant object and a rotational cap that is on the end of the utensil with an interior and exterior cap.

Referring to FIG. 4, a scented writing instrument 200 can comprise an elongate hollow body 202 having a distal tip 204 and a proximal end portion 206, with a longitudinal axis 208 extending between the distal tip 204 and the proximal end portion 206. A marking medium 250 is located at least partially inside the hollow body 202 and is extendible from the distal tip 204. The marking medium can be a pencil lead, a ball point pen tip, a felt marker, or other known marking medium.

A scented substrate 220 is located in the proximal end portion 206 of the hollow body 202. A cap assembly 260 comprising an inner cap 270 and an outer cap 280 is disposed over the proximal end portion 206. The inner cap 270 has at least one scent opening 271. An outer cap 280 also has at least one scent opening 281 and is disposed over the inner cap 270 and is rotatably coupled to the inner cap 270 such that rotation of the outer cap 280 relative to the inner cap 270 to a first position covers the at least one scent opening 271 and rotation of the outer cap 280 relative to the inner cap 270 to a second position that aligns the scent openings 271, 281 and exposes the at least one scent opening 271. The at least one scent opening 271 can be "throttled" by rotating the outer cap 280 about the longitudinal axis 208 in infinite positions between the first position and the second position to limit the amount of scent that can be emitted, as desired.

The scented substrate 220 is removable from body 202 to replace with a scented substrate having the same scent as or a different scent from scented substrate 220. The scented substrate is also configured so that a scented liquid can be applied to the scented substrate 220 to enhance the fragrance, such as after the writing instrument 200 had been in use over a period of time.

In order to be able to remove the scent substrate, the cap assembly 260, including the inner cap 270 and the outer cap 280 is removable from the body 202. In one embodiment, the inner cap 270 is threaded onto the hollow body 202 via threads 210 (shown in FIG. 4). Alternatively, the inner cap 270 can be press fit onto the hollow body 202 such that friction retains the inner cap 270 onto thee hollow body 202.

Figure 5:
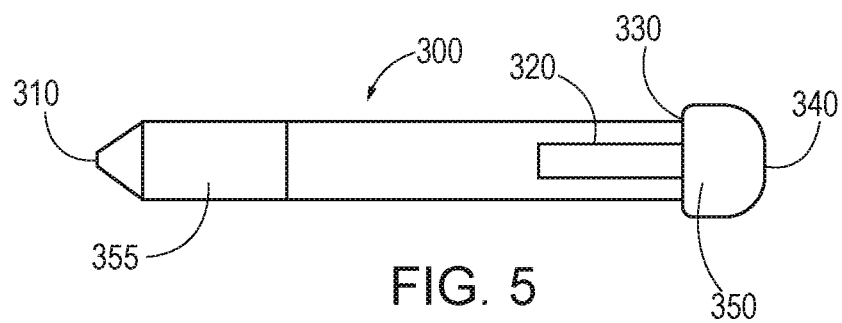
FIG. 5 is a section view of a utensil with a covering cap enclosing a fragrant object.

Referring to FIG. 5, utensil 300 allows fragrance 350 to emit from fragrant object 320 when covering cap 340 is detached. This time, there is no rotation necessary to allow fragrance 350 to emit or prevent fragrance 350 from emitting. When covering cap 340 is attached, fragrance 350 does not emit into the air, and when covering cap 340 is detached, fragrance 350 emits into the air. Utensil 300 has similar features as previous utensils containing marking material tip 310, and twist material 355.

Figure 6:
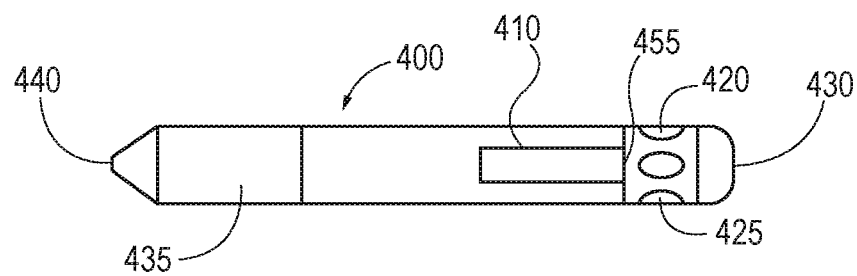
FIG. 6 is a section view of a utensil with a touchscreen device on the opposite end of the utensil tip end.

Referring to FIG. 6, utensil 400 contains touchscreen material 430 at the end of utensil 400. Touchscreen material 430 may be plastic, copper, indium tin oxide, among others. Touchscreen material 430 may be any shape, and is found at the opposite end of marking material 440. Marking material 440 is extended by twist material 435. Fragrance 455 emits from fragrant object 410 through utensil holes 420 and cap holes 425 when utensil holes 420 and cap holes 425 are aligned. Fragrance 455 does not emit when utensil holes 420 and cap holes 425 are not aligned as cap holes 425 are rotated to not be aligned.

Figure 7:
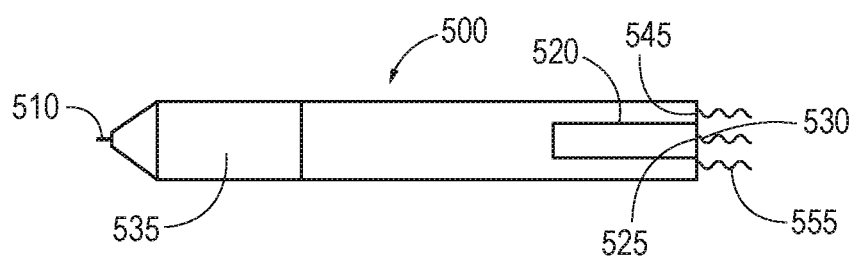
FIG. 7 is a section view of a utensil with the tip as the touchscreen device and an end-cap emitting fragrance on the opposite end of the touchscreen tip.

Referring to FIG. 7, utensil 500 contains touchscreen material 510 at the front of utensil 500. Touchscreen material 510 may be plastic, copper, indium tin oxide, among others. Touchscreen material 510 may be any shape, and is found at the opposite end of end-cap 530. Touchscreen material 510 is extended by twist material 535. Fragrance 555 emits from fragrant object 520 through end-cap holes 545 and utensil holes 525 when utensil holes 525 and end-cap holes 545 are aligned. Fragrance 555 does not emit when utensil holes 525 and end-cap holes 545 are not aligned as end-cap holes 545 are rotated to not be aligned with utensil holes 525.

Figure 8:
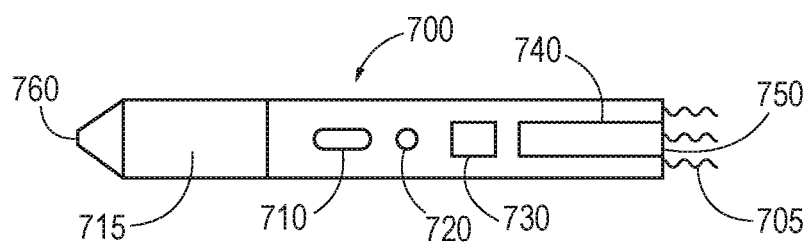
FIG. 8 is a section view of a utensil that emits fragrance powered by a battery.

Referring to FIG. 8, utensil 700 uses battery 710 to emit fragrance 705. Battery 710 powers utensil 700, activated by on off button 720. Microchip 730 prevents overcharge of battery 710. Fragrant object 740 emits fragrance 705 through end-cap 750. Marking material 760 is extended at front of utensil 700.

Figure 9:
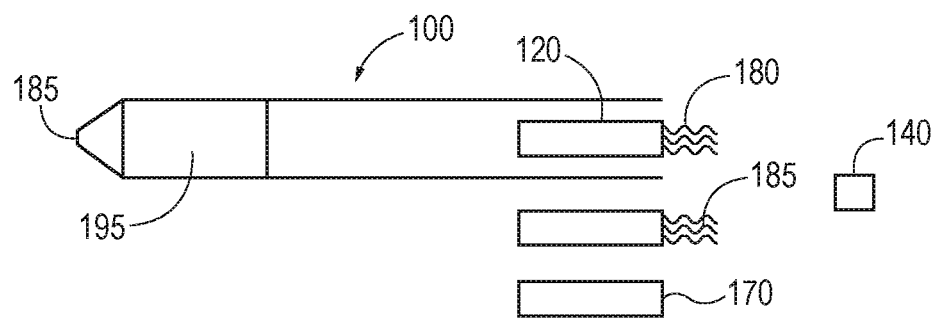
FIG. 9 is a section view of a utensil featuring extra fragrant objects.

Referring to FIG. 9, utensil 100 emits fragrance 180 from fragrant object 120. Additional fragrant objects 170 may replace fragrant object 120 so as to emit new fragrance 185. Detached cap 140 will then be attached to contain fragrance 180 and let fragrance 180 emit through the end of the attached cap 140. Marking material 185 will be extended by twisting twist material 195.

Figure 10:
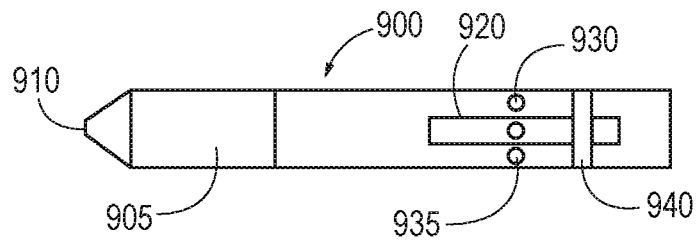
FIG. 10 is a section view of a utensil emitting or not emitting fragrance according to a sliding object.

Referring to FIG. 10, utensil 900 emits fragrance 935 from fragrant object 920 through utensil holes 930. These utensil holes 930 can be covered up to prevent fragrance 935 from emitting by sliding object 940 that can be pushed to cover the utensil holes 930. Sliding object 940 being pushed away from the utensil holes 930 allows fragrance 935 to emit. Marking material 910 is extended from twist material 905.

Figure 11:
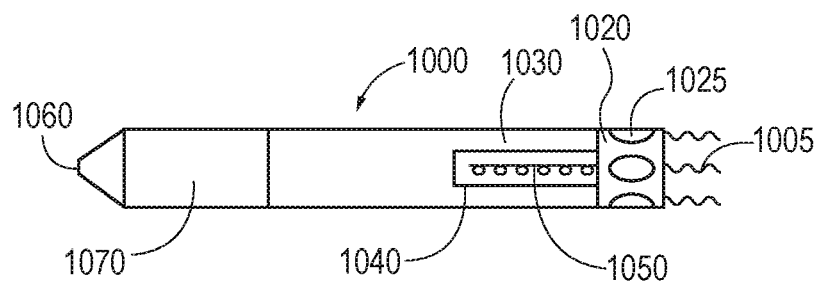

Referring to FIG. 11, utensil 1000 emits fragrance 1005 from fragrant object 1040 through side-cap 1020 that can be pushed downwards below notch 1030 by compressing spring 1050. When side-cap 1020 is below notch 1030, fragrance 1005 will not emit as side-cap holes 1025 are blocked by utensil 1000. Side-cap 1020 can then be pressed down more, further constricting spring 1050 so that spring 1050 pushes against side-cap 1020 with more force causing side-cap 1020 to move past notch 1030 and return to its previous location where side-cap holes 1025 are not blocked by utensil 1000 and fragrance 1005 is free to emit. Utensil 1000 extends marking material 1060 by twisting twist material 1070.

Figure 12:
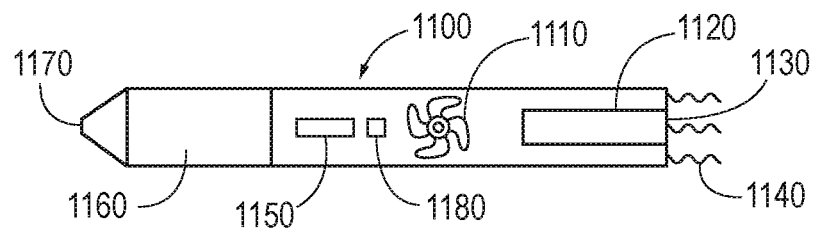
FIG. 12 is a section view of a utensil that emits fragrance propelled by a fan through an end-cap.

Referring to FIG. 12, utensil 1100 emits fragrance 1140 from fragrant object 1120 using fan 1110 powered by battery 1150. Fan 1100 is activated by on button 1180, and blows fragrance 1140 through end cap 1130. Utensil 1100 has marking material 1170 extended by twisting twist material 1160.

Figure 13:
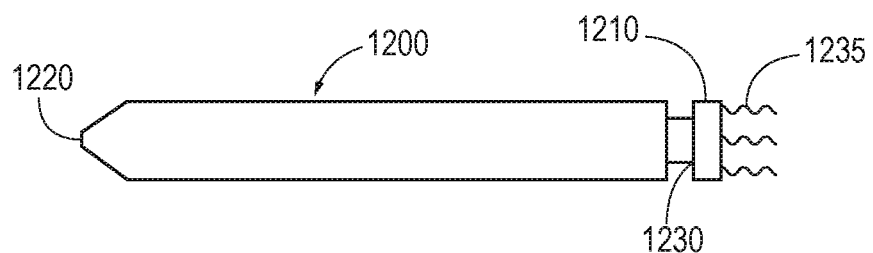
FIG. 13 is a section view of a utensil that emits fragrance from a scented eraser and extends marking material by pushing said eraser inward.

Referring to FIG. 13, utensil 1200 emits fragrance 1235 from fragrant eraser 1210. Fragrant eraser 1210 may be pushed downward (left in FIG. 15) pushing into connector object 1230 that pushes into shaft 1225 to push spring 1245 that extends marking material 1220 at opposite end of utensil 1200.

Figure 14:
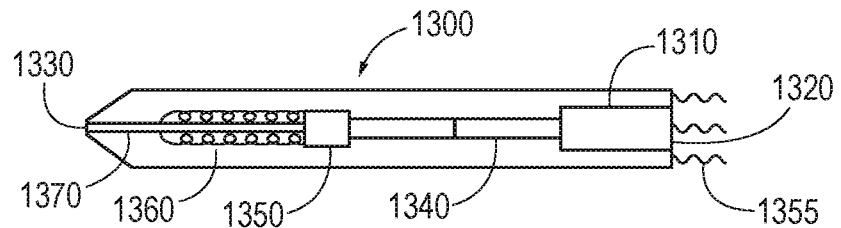
FIG. 14 is a section view of a utensil that emits fragrance at the end-cap and extends marking material by pushing end-cap inward.

Referring to FIG. 14, utensil 1300 emits fragrance 1355 from fragrant object 1310 through end cap 1320. End cap 1320 may be pushed downward (left in FIG. 14) to influence thrust tube 1340 that once pushed, will influence thrust device 1350 that once pushed, will influence spring 1360 that extends marking material 1370 past tip 1330.

The caps described herein can be used with any of the embodiments and not limited to the specific order that is described. While the invention is described above as a utensil, those skilled in the art will recognize the invention may be a pen, pencil, mechanical pencil, or any writing implement.

It will be further understood that various changes in the details, materials, and arrangements of the parts which have been described and illustrated in order to explain the nature of this invention may be made by those skilled in the art without departing from the scope of the invention as expressed in the following claims.

The invention claimed is:

1. A scented writing instrument comprising:
an elongate hollow body having a distal tip and a proximal end portion;
a marking medium located at least partially inside the hollow body and fixedly extending from the distal tip;
a scented substrate in the proximal end portion of the hollow body;
an inner cap disposed over the proximal end portion, the inner cap having at least one scent opening; and
an outer cap disposed directly over the inner cap such that rotation of the outer cap relative to the inner cap to a first position covers the at least one scent opening and rotation of the outer cap relative to the inner cap to a second position reveals the at least one scent opening.

2. The scented writing instrument according to claim 1, wherein the outer cap is rotatable between the first position and the second position.

3. The scented writing instrument according to claim 1, wherein the outer cap is removable from the body.

4. The scented writing instrument according to claim 1, wherein the scented substrate is removable from the body.

5. The scented writing instrument according to claim 1, wherein the scented substrate is configured to receive and absorb a scented liquid.

6. The scented writing instrument according to claim 1, wherein the inner cap and the outer cap comprise a cap assembly, the cap assembly being removable from the scented substrate.

7. The scented writing instrument according to claim 6, wherein the scented substrate is removable from the hollow body.

8. The scented writing instrument according to claim 6, wherein the cap assembly is press fit onto the body.

9. The scented writing instrument according to claim 6, wherein the hollow body comprises a longitudinal axis extending between the distal tip and the proximal portion and wherein the outer cap is configured to rotate about the longitudinal axis between a first position that covers the scent substrate and a second position that exposes the scent substrate.

10. The scented writing instrument according to claim 9, wherein the scent opening can be "throttled" by rotating the outer cap about the longitudinal axis in infinite positions between the first position and the second position.

11. The scented writing instrument according to claim 1, wherein the outer cap is press fit onto the hollow body.

* * * * *